United States Patent [19]

Sattler

[11] Patent Number: 5,653,989
[45] Date of Patent: Aug. 5, 1997

[54] WATER-IN OIL LOTION CONTAINING CORTICOSTEROID

[75] Inventor: Henning Sattler, Hamburg, Germany

[73] Assignee: Galderma S.A., Cham, Switzerland

[21] Appl. No.: 666,509

[22] PCT Filed: Dec. 22, 1994

[86] PCT No.: PCT/EP94/04288

§ 371 Date: Aug. 26, 1996

§ 102(e) Date: Aug. 26, 1996

[87] PCT Pub. No.: WO95/17883

PCT Pub. Date: Jul. 6, 1995

[30] Foreign Application Priority Data

Dec. 27, 1993 [DE] Germany .................. 43 44 697.3

[51] Int. Cl.$^6$ .................................................. A61K 7/48
[52] U.S. Cl. .................. 424/401; 424/405; 424/450; 424/455; 514/941; 514/943; 514/937
[58] Field of Search .................................. 424/450, 455; 514/12, 941, 943, 937

[56] References Cited

U.S. PATENT DOCUMENTS

| | | | |
|---|---|---|---|
| 4,252,796 | 2/1981 | Yu et al. | 424/179 |
| 4,347,238 | 8/1982 | Hollingsbee | 424/81 |
| 4,464,389 | 8/1984 | Dawson | 424/278 |
| 4,879,274 | 11/1989 | Kamiya et al. | 514/12 |
| 5,190,936 | 3/1993 | Laugier et al. | 424/450 |

*Primary Examiner*—Thurman K. Page
*Assistant Examiner*—Diedra Faulkner
*Attorney, Agent, or Firm*—Burns, Doane, Swecker & Mathis, L.L.P.

[57] ABSTRACT

The application is directed to a water-in-oil lotion containing hydrocotisone-21-acetate-17-propionate and one of four compositions containing a water-in-oil emulsion. The lotion is suitable for use on dry skin, it has good spreadability on large surface areas and it is dermatologically acceptable.

4 Claims, No Drawings

WATER-IN OIL LOTION CONTAINING CORTICOSTEROID

The present invention concerns a new type of lotion containing a corticosteroid as active ingredient.

Use is often made of creams as therapeutic vehicles containing corticosteroids. These creams incorporate either oil-in-water or water-in-oil emulsion systems.

For example, EP-A-0 217 146 discloses an oil-in-water cream containing a hydrocortisone diester. However, oil-in-water creams play a minor role in corticosteroid therapies, since most inflammatory processes are triggered when skin is dry. Accordingly, oil-in-water emulsions (containing water in the external phase of the emulsion) lend themselves to this application only in a limited manner.

Use is more often made of water-in-oil creams (containing oil in the external phase of the emulsion). Because of their thick consistency and, consequently, of the difficulty with which they are spread, they have the disadvantage of being unsuited to application on large surface areas. In addition, they leave an unctuous film on the skin, a cosmetically-adverse phenomenon. A water-in-oil emulsion-based cream containing hydrocortisone diester as active ingredient is, for example, described in Patent No. EP-A-0 217 141. "Stabilized" creams (water-in-oil emulsions) containing corticosteroids are described, for example, in U.S. Pat. No. 4,284,630.

These two problems, i.e., poor spreadability on large surface areas and cosmetic unacceptableness, also apply to a greater degree to a third type of topical preparation, i.e., creams such as ointments having a vaseline/paraffin base (fatty ointments). In addition to these problems, these preparations soil linen and clothing that has come into contact with skin treated with them.

A fourth type of vehicle intended for corticosteroid therapy consists of liquid oil-in-water liquid emulsions, and thus, lotions. The scope of application of these products is similar to that of oil-in-water creams. Oil-in-water lotions nevertheless exhibit the same basic problem as oil-in-water creams. They are not suitable for use on dry skin, which is most often encountered when these products are indicated. Consequently, the field of application of these lotions is extremely limited, despite their general aptitude for application on large surface areas.

Tinctures and tinctures solidified using gelling agents form a fifth type of base for corticosteroids. In this case, these tinctures are solutions, most often ethanol-, isopropanol/propylene glycol-, or polyethylene glycol/water-based. They are often, but erroneously, termed lotions, even though they are not constituted by emulsion systems. While these lotions contain, in addition, a surface-active substance, this substance is used only to solubilize the minimally-soluble corticosteroid. Such a tincture, is, for example, described (as a "lotion") in patent EP-A-0 292 893.

The preceding description shows that, to date, there is no vehicle for corticosteroids which meets the following requirements:

suitability for use on dry skin;
spreadability on large surface areas;
dermatological acceptability.

Water-in-oil lotions alone lend themselves to these purposes. To date, they have not been used in corticosteroid therapy. Even in the cosmetic industry, water-in-oil lotions tend to separate during storage into an oil and an aqueous phase. Consequently, they cannot be produced by "diluting" a water-in-oil cream with water. To obtain a water-in-oil lotion, a complex combination of multiple emulsifiers with specially-adapted lipophilic compounds proves necessary.

Use must be made of combinations of emulsifiers, because it is hardly possible to produce a stable water-in-oil lotion based on only one of the emulsifiers indicated above. Water-in-oil emulsifiers (or mixtures thereof) constitute new substances that are particularly well-adapted to water-in-oil lotions. They are not identical to the emulsifiers widely used in water-in-oil creams, such as sorbitan oleates and sorbitan stearates (Span (R) products). The latter (see U.S. Pat. No. 4,284,630) can be used solely for preparing water-in-oil creams.

As regards a water-in-oil lotion of this kind containing a corticosteroid as active ingredient, consideration must be given to the fact that most emulsifiers and stabilizers potentially usable in water-in-lotions tend to cause decomposition of the corticosteroid they contain. The stability during storage of the active substance necessary for a therapeutic product is thus rendered doubtful. The phrase "necessary stability during storage" signifies that the water-in-oil lotion as well as the active substance exhibit the preservability required for a drug, and thus a life of at least 3 years, even at high temperatures (greater than 30° C.).

Patent No. DE-A-28 26 257 discloses the corticosteroid hydrocortisone-21-acetate-17-alpha-propionate.

The invention is intended to propose a water-in-oil lotion containing hydrocortisone-21-acetate-17-alpha-propionate, exhibiting good stability of the liquid emulsion, while at the same time providing good preservability of the active substance during storage and proving optimally suitable for therapy using corticosteroids in cases of dry skin and for application on large surface areas.

This purpose is achieved using water-in-oil lotions having the following compositions A, B, C, or D with combinations of the water-in-oil emulsifiers a) to d).

A.

| Emulsifier combination a) | % by weight |
| --- | --- |
| $a_1$: methoxypolyethylene glycol/dodecyl glycol polymer | 1–10 |
| $a_2$: hydroxyoctacosanyl hydroxy stearate | 0.5–10 |
| $a_3$: polyethylene glycol/dodecylglycol copolymer | 1–10 |
| esters of fatty acids and/or fatty alcohols | 1–30 |
| liquid paraffin | 1–30 |
| glycerine or sorbitol solution (70% by weight) | 1–10 |
| hydrocortisone-21-acetate-17-propionate | 0.001–3 |
| preservative | 0–2.5 |
| water | 50–85 |

B.

| Emulsifier combination b) | |
| --- | --- |
| $b_1$: esters of fatty acids saturated with glycerol sorbitan | 0.5–10 |
| $b_2$: polyethoxylated fatty acids | 1–7.5 |
| esters of fatty acids and/or fatty alcohols | 1–30 |
| liquid paraffin | 1–30 |
| glycerine or sorbitol solution (70% by weight) | 1–10 |
| magnesium sulfate, heptahydrate | 0.1–2 |
| hydrocortisone-21-acetate-17-propionate | 0.001–3 |
| preservative | 0–2.5 |
| water | 50–85 |

C.

| Emulsifying combination c) | |
| --- | --- |
| $c_1$: polyoxypropylene-polyoxyethylene-glycerol-sorbitan-hydroxyisostearate | 0.5–10 |
| $c_2$: polyethoxylated fatty acids | 0.5–7.5 |
| esters of fatty acids and/or fatty alcohols | 1–30 |
| liquid paraffin | 1–30 |
| glycerine or sorbitol solution (70% by weight) | 1–10 |
| magnesium sulfate, heptahydrate | 0.1–2.0 |
| hydrocortisone-21-acetate-17-propionate | 0.001–3 |
| preservative | 0–2.5 |
| water | 50–85 |

3

-continued

| D. Emulsifying combination d) | |
|---|---|
| $d_1$: glycerol sorbitan oleostearate | 0.5–7.5 |
| $d_2$: polyethoxylated fatty acids | 0.5–10 |
| esters of fatty acids and/or fatty alcohols | 1–30 |
| liquid paraffin | 1–30 |
| glycerine or sorbitol solution (70% by weight) | 1–10 |
| magnesium sulfate, heptahydrate | 0.1–2 |
| hydrocortisone-21-acetate-17-propionate | 0.001–3 |
| preservative | 0–2.5 |
| water | 50–85 |

Each of the compositions A to D may, as required, contain additives, and, in addition to the emulsifying combination indicated, one or several of the other constituents $a_1$ to $d_2$, or one or several of the emulsifying combinations a) to d) mentioned above.

In the lotions containing compositions A, B, C, or D, the water-in-oil emulsifying combinations a) to d) are composed of emulsifiers, stabilizers, thickening agents, and complex emulsifying systems $a_1$, $a_2$, etc. to $d_1$, $d_2$ as constituents.

Constituent $a_1$ is preferably a non-ionic water-in-oil emulsifier containing approximately 22 ethylene glycol repeating structures. These emulsifiers are sold under the tradename Elfacos E 200 (Akzo Chemie, The Netherlands).

The constituent $a_2$ acts as a consistency regulator. These products are sold under the tradename Elfacos C26 (Akzo Chemie, The Netherlands).

The constituent $a_3$ is preferably a non-ionic water-in-oil emulsifier having approximately 20 to 45 ethylene glycol repeating structures and an HLB value of about 7. These emulsifiers are sold under the tradenames Elfacos ST 9 and Ellacos ST 37 (Akzo Chemie, The Netherlands). Furthermore, they are described in the literature mentioned above.

Constituent $b_1$ is a non-ionic water-in-oil emulsifier preferably having a molecular weight of about 630, and HLB value of about 4.5, and a wax-like consistency. These products are sold under the tradename Arlacel 986 (ICI Europa Ltd., Belgium).

Constituent $b_2$ is preferably a non-ionic saturate water-in-oil emulsifier having a molecular weight of approximately 1,245 and an HLB value of about 6.4. Such products are sold, most notably, under the tradename Arlacel 989 (ICI) or Cremophor WO 7 (BASF).

Constituent $b_2$ corresponds to constituents $c_2$ and $d_2$.

Constituent $c_1$ is a non-ionic saturate water-in-oil emulsifier. These products are also sold under the tradename Arlacel 780 (ICI).

The preferred esters of fatty acids include isopropyl palmitate, isopropyl myristate, isopropyl isostearate, myristyl myristate, 2-cetylhexyl palmitate (Cegesoft sold by the Henkel Company), isooctyl stearate (Cetiol 868, sold by the Henkel Company), the decylic ester of oleic acid (Cetiol V), and the cetyl ester of palmitic acid (Cutina CP, sold by the Henkel company).

The preferred fatty alcohols include myristic alcohol, cetyl alcohol, stearyl alcohol, cetostearyl alcohol, behenyl alcohol, and 2-octyldodecanol (Eutanol G).

The paraffin chosen is preferably a highly liquid paraffin, as required in combination with a semi-solid paraffin (vaseline), a solid paraffin, or microwaxes. Linear and branched paraffins are especially preferred.

One suitable sorbitol solution is, for example, a 70% aqueous solution. Products of this type are sold, most notably, under the names "Kadon F," "Karion F flüssig SK," or "Karion F flüssig kosmetik" (E. Merck, Germany).

4

The lotions preferably contain hydrocortisone-21-acetate-17-propionate in a concentration of 0.001 to 1% by weight, in particular from 0.01 to 0.3 by weight, always in relation to the total weight.

Special preference is given to hydrocortisone-21-acetate-17-alpha-propionate in a proportion of 0.025 to 0.2% by weight, in particular approximately 0.13% by weight, always in relation to the total weight of the lotion.

Special preference is accorded to lotions incorporating the following constituents and, as required, additives.

| A'. Emulsifier combination a) | % by weight |
|---|---|
| $a_1$: methoxypolyethylene glycol/dodecylglycol polymer | 2–7.5 |
| $a_2$: hydroxyoctacosanylhydroxystearate | 1–5 |
| $a_3$: polyethylene glycol/dodecylglycol copolymer | 2–7.5 |
| esters of fatty acids | 1–15 |
| liquid paraffin | 1–15 |
| glycerine or sorbitol solution (70% by weight) | 1–10 |
| hydrocortisone-21-acetate-17-propionate | 0.01–2.5 |
| preservative | 0.2–1.5 |
| water | 60–80 |

| B'. Emulsifier combination b) | |
|---|---|
| $b_1$: esters of fatty acids saturated with glycerol sorbitan | 2–7.5 |
| $b_2$: polyethoxylated fatty acids | 1–5 |
| esters of fatty acids | 1–15 |
| liquid paraffin | 1–15 |
| glycerine or sorbitol solution (70% by weight) | 1–10 |
| magnesium sulfate, heptahydrate | 0.3–1.5 |
| hydrocortisone-21-acetate-17-propionate | 0.01–2.5 |
| preservative | 0.2–1.5 |
| water | 60–80 |

| C'. Emulsifying combination c) | |
|---|---|
| $c_1$: polyoxypropylene-polyoxyethylene-glycerol-sorbitan-hydroxyisostearate | 2–7.5 |
| $c_2$: polyethoxylated fatty acids | 1–5 |
| esters of fatty acids | 1–15 |
| liquid paraffin | 1–15 |
| glycerine or sorbitol solution (70% by weight) | 1–10 |
| magnesium sulfate, heptahydrate | 0.3–1.5 |
| hydrocortisone-21-acetate-17-propionate | 0.01–2.5 |
| preservative | 0.2–1.5 |
| water | 60–80 |

| D'. Emulsifying combination d) | |
|---|---|
| $d_1$: glycerol sorbitan oleostearate | 1–5 |
| $d_2$: polyethoxylated fatty acids | 2–8 |
| esters of fatty acids | 1–15 |
| liquid paraffin | 1–15 |
| glycerine or sorbitol solution (70% by weight) | 1–10 |
| magnesium sulfate, heptahydrate | 0.3–1.5 |
| hydrocortisone-21-acetate-17-propionate | 0.01–2.5 |
| preservative | 0.2–1.5 |
| water | 60–80 |

To adjust the pH to a preferred value of 4 to 5, the lotion according to the invention may contain small quantities of acidic additives, for example from about 0.01 to about 5% by weight. To this end, carboxylic acids such as succinic acid, lactic acid, citric acid, or phosphoric acid and the salts thereof are suitable for use as buffers.

Preservative and stabilizers can also be added. Suitable substances include parabene, benzalkonium chlorides, p-chloro-m-cresol, benzoic acid, sorbic acid, phenoxyethanol, benzyl acid, butyl hydroxyanisol and butyl hydroxytoluene, tocopherol acetate, ascorbyl palmitate, and mixtures thereof. These substances may be added in a proportion of from 0.01 to 2.5% by weight.

Emulsifiers suitable for water-in-oil lotions containing corticosteroids consist partially of very complex compositions having low HLB values, as well as of mixtures thereof. The choice of emulsifiers was made in order to produce a water-in-oil lotion proving stable for several years at high temperatures and compatible with the respective active ingredients to obtain stabilization of the active ingredients during the period indicated.

The fatty phase of the water-in-oil lotion consists, for example, of a balanced mixture of liquid paraffins having a linear or branched chain, of natural and synthetic esters, of fatty acids having a linear or branched chain, whether saturated or unsaturated with monovalent or polyvalent alcohols (for example, isopropyl palmitate, isopropyl myristate, isopropyl stearate, isopropyl isostearate, myristyl myristate, cetyl palmitate, oleyl oleate, triglycerides having a medium chain, peanut oil, olive oil, castor oil, hydrogenated castor oil), fatty acids (for example, linoleic acid, oleic acid), and fatty alcohols (for example, myristic alcohol, cetostearyl alcohol), octyl dodecanol, and squalene in a proportion of 1 to 30% by weight, for example.

The lotions according to the invention may contain other additives.

The aqueous phase contains, for example, polyvalent alcohols (for example, glycerine, propylene glycol, 1,3-butylene glycol, and polyethylene glycols), saccharide alcohols (for example, sorbitol and xylitol), lecithins (for example, soy lecithin and ovolecithin), or phosphatidyl choline and dipalmitoyl phosphatidyl choline compounds, for example in a proportion of 1 to 10% by weight.

With the new lotion according the invention, the invention discloses a new water-in-oil lotion containing hydrocortisone-17-propionate-21-acetate which is characterized by a good activity level, high dermatological acceptability, and a high degree of stability during storage.

In comparison with a water-in-oil cream, the water-in-oil lotion has the significant advantage of being rapidly absorbed by the skin and of leaving no bothersome unctuous cream, contrary to the cream and regardless of the type of emulsion.

To prepare the lotion, the fatty phase constituents, such as paraffin, isopropyl esters of fatty acids, and the combination of emulsifiers are melted and heated to high temperature, for example of between 60° and 80°, in conventional fashion. Sorbitol, glycerine, and magnesium sulfate, along with the constituents of the aqueous phase, are dissolved in water at high temperature. The phases are combined and emulsified. The active ingredient is added at lower temperature, for example between 40° and 60°. Next, the mass is allowed to cool while stirring.

The active substance is very effectively absorbed by the lotion according to the invention, which exhibits excellent stability under storage. It is used, for example, to treat eczema, dermatitis, psoriasis, and intimation.

To heal or treat these disorders, the lotion according to the invention may be applied topically on the affected areas. The quantity of lotion applied varies depending on the concentration of the active ingredient. In general, a suitable quantity is applied to the affected area several times daily, depending on the seriousness of the disorder requiring treatment.

Unless otherwise indicated, all quantities, portions, and percentages are applied in relation to the total weight or quantity or to the total weight of the preparations.

The following examples are intended to illustrate the invention, but in a non-limiting fashion.

Water-in-oil lotions are prepared in the following way: The fatty phase constituents, such as paraffin, fatty acid esters, and the emulsifier combination are heated to approximately 80° C. in a mixer-homogenizer which can be placed under a vacuum. Next, the aqueous phase constituents, such as sorbitol, glycerine, and magnesium sulfate, along with the acids and buffering agents, are dissolved in a corresponding proportion in water at a temperature of about 80° C., and the aqueous phase is added to the fatty phase in the mixer. The mixture is cooled in a vacuum to about 40° C. and homogenized while stirring. The active substance is added at this temperature and the preparation is cooled to about 25° C. while stirring and under a vacuum. The preservatives are dissolved, depending on their physical and chemical properties, either in the fatty phase at approximately 80° C., in the aqueous phase at approximately 80°, or added to the preparation at about 40° C.

In the following examples, hydrocortisone-21-acetate-17-propionate is used as the corticosteroid.

EXAMPLE 1

The water-in-oil lotion was prepared by using the following constituents:

|  | % by weight |
| --- | --- |
| methoxypolyethylene glycol/dodecylglycol copolymer (Elfacos E 200) | 3.0 |
| hydroxyoctacosanyl hydroxy stearate (Elfacos C 26) | 2.5 |
| polyethylene glycol/dodecylglycol copolymer (Elfacos St 9) | 5.0 |
| isopropyl palmitate | 11.0 |
| synthetic squalene | 2.0 |
| liquid paraffin | 10.0 |
| 70% sorbitol (Karion F) | 1.0 |
| hydrocortisone-21-acetate-17-propionate | 0.200 |
| butyl hydroxytoluene | 0.05 |
| benzyl alcohol | 0.5 |
| phenoxyethanol | 0.5 |
| citric acid | q.s. (to adjust the pH to 4–5) |
| demineralized water | to 100.00 |

The preparation was produced using the procedure detailed above. The preservative, phenoxyethanol, was dissolved in the aqueous phase, and the anti-oxidant, butyl hydroxytoluene, was dissolved in the fatty phase. The active substance, hydrocortisoneaceponate, was dissolved in benzylic alcohol and added to the lotion at a temperature of approximately 40° C.

EXAMPLE 2

A water-in-oil lotion was prepard by using the constituents listed below:

|  | % by weight |
| --- | --- |
| fatty acid ester saturated with glycerol sorbitan (Arlacel 986) | 1.5 |
| polyethoxylated fatty acids (Arlacel 989 or Cremophor WO 7) | 3.0 |
| isopropylmyristate | 5.0 |
| liquid paraffin | 11.0 |
| 1,3-butylene glycol | 3.0 |
| magnesium sulfate, heptahydrate | 0.5 |
| hydrocortisone-21-acetate-17-propionate | 0.127 |
| benzyl alcohol | 1.0 |
| demineralized water | to 100.00 |

EXAMPLE 3

A water-in-oil lotion was prepard by using the constituents listed below:

| | % by weight |
|---|---|
| polyoxypropylene-polyoxyethylene-glycerol-sorbitan hydroxyisostearate (Arlacel 780) | 4.0 |
| polyethoxylated fatty acids (Arlacel 989) | 2.0 |
| isopropyl myristate | 7.0 |
| octyldodecanol | 5.0 |
| liquid paraffin | 13.5 |
| glycerine | 2.5 |
| 70% sorbitol (Karion F) | 2.5 |
| hydrocortisone-21-acetate-17-propionate | 0.127 |
| phosphatidyl choline | 3.0 |
| benzalkonium chloride | 0.25 |
| lactic acid | q.s. (to adjust the pH to 4–5) |
| demineralized water | to 100.00 |

EXAMPLE 4

| | % by weight |
|---|---|
| glycerol sorbitan oleostearate (Arlacel 481, ICI Company) | 2.0 |
| polyethoxylated fatty acids (Arlacel 989, ICI Company) | 6.0 |
| decyl oleate (Cetiol C, Henkel Company) | 15.0 |
| branched-chain paraffin (Arlamol HD, ICI Company) | 8.0 |
| microwax | 1.0 |
| glycerine | 4.0 |
| magnesium sulfate, heptahydrate | 0.70 |
| sodium salt of sorbic acid | 0.20 |
| hydrocortisone-21-acetate-17-propionate | 0.05 |
| diammonium hydrogenocitrate | 0.10 |
| citric acid | q.s. (to adjust the PH to 4–5) |
| demineralized water | to 100.00 |

I claim:

1. A water-in-oil lotion comprising hydrocortisone-21-acetate-17-propionate and a composition selected from the group consisting of A, B, C, and D each consisting of water-in-oil emulsifiers a) to d):

wherein A. is:

| Emulsifier combination a) | % by weight |
|---|---|
| $a_1$:methoxypolyethylene glycol/dodecylglycol polymer | 1–10 |
| $a_2$:hydroxyoctacosanyl hydroxystreate | 0.5–10 |
| $a_3$:polyethylene glycol/dodecylglycol copolymers | 1–10 |
| esters of fatty acids and/or fatty alcohols | 1–30 |
| liquid paraffin | 1–30 |
| glycerine or sorbitol solution (70% by weight) | 1–10 |
| hydrocortisone-21-acetate-17-propionate | 0.001–3 |
| preservative | 0–2.5 |
| water | 50–85 | wherein B. is:

| Emulsifier combination b) | % by weight |
|---|---|
| $b_1$:esters of fatty acids saturated with glycerol sorbitan | 0.5–10 |
| $b_2$:polyethoxylated fatty acids | 1–7.5 |
| esters of fatty acids and/or fatty alcohols | 1–30 |
| liquid paraffin | 1–30 |
| glycerine or sorbitol solution (70% by weight) | 1–10 |
| magnesium sulfate, heptahydrate | 0.1–2 |
| hydrocortisone-21-acetate-17-propionate | 0.001–3 |
| preservative | 0–2.5 |
| water | 50–85 | wherein C. is:

| Emulsifier combination c) | |
|---|---|
| $c_1$:polyoxypropylene-polyoxyethylene-glycerol-sorbitan-hydroxyisostearate | 0.5–10 |
| $c_2$:polyethoxylated fatty acids | 0.5–7.5 |
| esters of fatty acids and/or fatty alcohols | 1–30 |
| liquid paraffin | 1–30 |
| glycerine or sorbitol solution (70% by weight) | 1–10 |
| magnesium sulfate, heptahydrate | 0.1–2 |
| hydrocortisone-21-acetate-17-propionate | 0.001–3 |
| preservative | 0–2.5 |
| water | 50–85 | wherein D. is:

| Emulsifier combination d) | |
|---|---|
| $d_1$ glycerol sorbitan oleostearate | 0.5–7.5 |
| $d_2$:polyethoxylated fatty acids | 0.5–10 |
| esters of fatty acids and/or fatty alcohols | 1–30 |
| liquid paraffin | 1–30 |
| glycerine or sorbitol solution (70% by weight) | 1–10 |
| magnesium sulfate, heptahydrate | 0.1–2.0 |
| hydrocortisone-21-acetate-17-propionate | 0.001–3 |
| preservative | 0–2.5 |
| water | 50–85 | in combination with cosmetically acceptable additives, and, in addition to the emulsifying combination indicated, one or a of the other constituents $a_1$ to $d_2$ or one or several of the emulsifying combinations a) to d).

2. The lotion according to claim 1, containing the following constituents:

A'

| Emulsifier combination a) | % by weight |
|---|---|
| $a_1$: methoxypolyethlene glycol/dodecyglycol polymer | 2–7.5 |
| $a_2$: hydroxyoctacosanyl hydroxystreate | 1–5 |
| $a_3$: polyethylene glycol/dodecylglycol copolymers | 2–7.5 |
| esters of fatty acids and/or fatty alcohols | 1–15 |
| liquid paraffin | 1–15 |
| glycerine or sorbitol solution (70% by weight) | 1–10 |
| hydrocortisone-21-acetate-17-propionate | 0.01–2.5 |
| preservative | 0.2–1.5 |
| water | 60–80 |

B'

| Emulsifier combination b) | |
|---|---|
| $b_1$: esters of fatty acids saturated with glycerol sorbitan | 2–7.5 |
| $b_2$: polyethoxylated fatty acids | 1–5 |
| esters of fatty acide and/or fatty alcohols | 1–15 |
| liquid paraffin | 1–15 |
| glycerine or sorbitol solution (70% by weight) | 1–10 |
| magnesium sulfate, heptahydrate | 0.3–1.5 |
| hydrocortisone-21-acetate-17-propionate | 0.01–2.5 |
| preservative | 0.2–1.5 |
| water | 60–80 |

C'

| Emulsifier combination c) | |
|---|---|
| $c_1$: polyoxypropylene-poloxyethylene-glycerol-sorbitan-hydroxyisostearate | 2–7.5 |
| $c_2$: polyethoxylated fatty acids | 1–5 |
| esters of fatty acids and/or fatty alcohols | 1–15 |
| liquid paraffin | 1–15 |
| glycerine or sorbitol solution (70% by weight | 1–10 |
| magnesium sulfate, heptahydrate | 0.3–1.5 |
| hydrocortisone-21-acetate-17-propionate | 0.01–2.5 |
| preservative | 0.2–1.5 |

-continued

| | |
|---|---|
| water | 60–80 |

D'
Emulsifier combination d)

| | |
|---|---|
| $d_1$ glycerol sorbitan oleostearate | 1–5 |
| $d_2$: polyethoxylated fatty acids | 2–8 |
| esters of fatty acids and/or fatty alcohols | 1–15 |
| liquid paraffin | 1–15 |
| glycerine or sorbitol solution (70% by weight) | 1–10 |
| magnesium sulfate, heptahydrate | 0.3–1.5 |
| hydrocortisone-21-acetate-17-propionate | 0.01–2.5 |
| preservative | 0.2–1.5 |
| water | 60–80 |

3. The lotion according to claim 1, wherein said lotion contains from 0.0025 to 0.2% by weight hydrocortisone-21-acetate-17-alpha-propionate (hydrocortisoneaceponate).

4. The lotion according to claim 1, having the following composition:

| | % by weight |
|---|---|
| fatty acid ester saturated with glycerol sorbitan (Arlacel 986) | 1.5 |
| polyethoxylated fatty acids (Arlacel 989 or Cremophor WO7) | 3.0 |
| isopropyl myristate | 5.0 |
| liquid paraffin | 11.0 |
| 1,3-butylene glycol | 3.0 |
| magnesium sulfate, heptahydrate | 0.5 |
| hydrocortisone-21-acetate-17-propionate | 0.127 |
| benzyl alcohol | 1.0 |
| demineralized water | to 100.00 |

\* \* \* \* \*